United States Patent
Anderson et al.

(10) Patent No.: US 8,011,507 B2
(45) Date of Patent: Sep. 6, 2011

(54) METHODS AND APPARATUS FOR COLLECTING AND DISPOSING OF SHARPS

(75) Inventors: Barry Anderson, Sheboygan, WI (US); Joseph Hand, Sheboygan Falls, WI (US)

(73) Assignee: Bemis Manufacturing Company, Sheboygan Falls, WI (US)

( * ) Notice: Subject to any disclaimer, the term of this patent is extended or adjusted under 35 U.S.C. 154(b) by 309 days.

(21) Appl. No.: 12/257,812

(22) Filed: Oct. 24, 2008

(65) Prior Publication Data

US 2009/0108007 A1      Apr. 30, 2009

Related U.S. Application Data

(60) Provisional application No. 61/000,212, filed on Oct. 24, 2007.

(51) Int. Cl.
*B03B 1/00* (2006.01)
(52) U.S. Cl. .............. 206/366; 241/65; 209/11
(58) Field of Classification Search ............ 206/366; 422/1, 22, 307; 241/65, 99; 209/11
See application file for complete search history.

(56) References Cited

U.S. PATENT DOCUMENTS

| | | | |
|---|---|---|---|
| 3,476,506 A | | 11/1969 | Andersen et al. |
| 3,736,933 A | * | 6/1973 | Szabo ............ 604/200 |
| 3,892,706 A | | 7/1975 | Jetzer |
| 4,409,029 A | | 10/1983 | Larker et al. |
| 4,434,074 A | | 2/1984 | Fox et al. |
| 4,552,720 A | | 11/1985 | Baker, Sr. et al. |
| 4,657,139 A | * | 4/1987 | Hanifl ............ 220/821 |
| 4,662,516 A | * | 5/1987 | Baker et al. ........ 206/363 |
| 4,756,681 A | | 7/1988 | Unger et al. |
| 4,834,917 A | | 5/1989 | Ramm et al. |
| 4,860,958 A | | 8/1989 | Yerman |
| 4,940,157 A | | 7/1990 | Inagaki |
| 4,992,217 A | | 2/1991 | Spinello |
| 5,003,892 A | * | 4/1991 | Bricken ........ 110/346 |
| 5,078,924 A | | 1/1992 | Spinello |
| 5,124,126 A | * | 6/1992 | Ripp ............ 422/26 |

(Continued)

FOREIGN PATENT DOCUMENTS

EP      0430898      6/1991

(Continued)

OTHER PUBLICATIONS

PCT/US2008/081099 International Search Report dated Jul. 13, 2009 (5 pages).

(Continued)

*Primary Examiner* — Jacob K Ackun, Jr.
(74) *Attorney, Agent, or Firm* — Michael Best & Friedrich LLP (57) ABSTRACT

A receptacle for holding a meltable sharps container during a sterilization process in which the meltable sharps container and any contained sharps are heated. The receptacle includes a side wall and a bottom wall having respective interior surfaces defining a space for receiving the meltable sharps container. The receptacle also includes a plurality of recessed areas in the interior surface of the bottom wall, and a plurality of elevated areas on the interior surface of the bottom wall, whereby as the sharps container melts, material from the sharps container flows into the recessed areas and the elevated areas hold the contained sharps above the recessed areas, so as to inhibit the contained sharps from protruding through the melted sharps container.

22 Claims, 10 Drawing Sheets

U.S. PATENT DOCUMENTS

| | | | |
|---|---|---|---|
| 5,193,740 A * | 3/1993 | Newborough et al. | 229/242 |
| 5,213,758 A * | 5/1993 | Kawashima et al. | 422/21 |
| 5,350,562 A * | 9/1994 | Anthony | 422/1 |
| 5,401,444 A | 3/1995 | Spinello | |
| 5,413,243 A | 5/1995 | Bemis et al. | |
| 5,441,622 A * | 8/1995 | Langford | 204/273 |
| 5,447,685 A * | 9/1995 | Sievert et al. | 422/22 |
| 5,605,245 A | 2/1997 | Bemis et al. | |
| 5,848,693 A | 12/1998 | Davis et al. | |
| 5,866,085 A | 2/1999 | Yelvington | |
| 5,972,291 A | 10/1999 | Healy et al. | |
| 6,010,444 A * | 1/2000 | Honeycutt et al. | 588/255 |
| 6,715,628 B1 | 4/2004 | Nichols et al. | |
| 2004/0001783 A1 * | 1/2004 | Bowen | 422/292 |
| 2006/0045797 A1 * | 3/2006 | Frazier | 422/22 |
| 2007/0224077 A1 * | 9/2007 | Cox et al. | 422/1 |
| 2010/0278688 A1 * | 11/2010 | Tanaka et al. | 422/26 |

FOREIGN PATENT DOCUMENTS

| | | |
|---|---|---|
| EP | 0697271 | 2/1996 |
| FR | 2767670 | 3/1999 |
| WO | 03/070394 | 8/2003 |

OTHER PUBLICATIONS

PCT/US2008/081099 International Preliminary Report on Patentability dated May 6, 2010 (12 pages).

* cited by examiner

METHODS AND APPARATUS FOR COLLECTING AND DISPOSING OF SHARPS

RELATED APPLICATION(S)

This application claims priority to U.S. Provisional Patent Application No. 61/000,212; filed on Oct. 24, 2007.

BACKGROUND

The present invention relates to apparatus and methods for collecting and disposing of sharps.

Traditionally, hazardous medical waste (e.g., syringes or tubes with needles, scalpels, etc.) has been contained in plastic sharps containers and then sterilized by heating the sharps container. Often sharps (e.g., needles, scalpels, knives, etc.) end up settling at the bottom of the melting sharps container. If the sharps are allowed to sit in this position during the cooling of the plastic, the tips of the metal sharps will tend to protrude from the plastic. In some cases, sharps end up protruding about 0.02 inches to about 0.03 inches, which is enough for a user to contact and draw blood. This becomes a potential hazard to anyone handling the block of plastic and sharps.

SUMMARY

In one aspect, the invention provides a receptacle for holding a meltable sharps container during a sterilization process in which the meltable sharps container and any contained sharps are heated. The receptacle includes a side wall and a bottom wall having respective interior surfaces defining a space for receiving the meltable sharps container. The receptacle also includes a plurality of recessed areas in the interior surface of the bottom wall, and a plurality of elevated areas on the interior surface of the bottom wall, whereby as the sharps container melts, material from the sharps container flows into the recessed areas and the elevated areas hold the contained sharps above the recessed areas, so as to inhibit the contained sharps from protruding through the melted sharps container.

In another aspect, the invention provides a method of collecting and disposing of sharps. The method includes collecting the sharps in a meltable sharps container having a bottom, providing a receptacle including a side wall and a bottom wall having respective interior surfaces defining a space, a plurality of recessed areas in the interior surface of the bottom wall, and a plurality of elevated areas on the interior surface of the bottom wall, placing the sharps container in the space of the receptacle so that the bottom of the sharps container is above or supported by the elevated areas, and melting the sharps container in the receptacle such that as the sharps container melts. Material from the sharps container flows into the recessed areas and the elevated areas hold the sharps above the recessed areas, so as to inhibit the sharps from protruding through the melted sharps container. The method also includes removing the melted sharps container from the receptacle, and disposing of the melted sharps container and sharps.

In another aspect, the invention provides a sharps container to be at least partially melted to sterilize the sharps container and any contained sharps. The sharps container includes a body defining a space for receiving the sharps, and including an upper portion and a lower portion that melts at a slower rate than the upper portion such that as the sharps container is heated. The upper portion melts so as to flow around the sharps and the lower portion inhibits the sharps from protruding through the lower portion.

In another aspect, the invention provides a method of collecting and disposing of sharps. The method includes providing a sharps container including a body having an upper portion and a lower portion, collecting the sharps in the sharps container, and heating the sharps container in a receptacle such that the lower portion melts at a slower rate than the upper portion and thereby inhibits the sharps from protruding through the lower portion. The method also includes removing the melted sharps container from the receptacle, and disposing of the melted sharps container and sharps.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
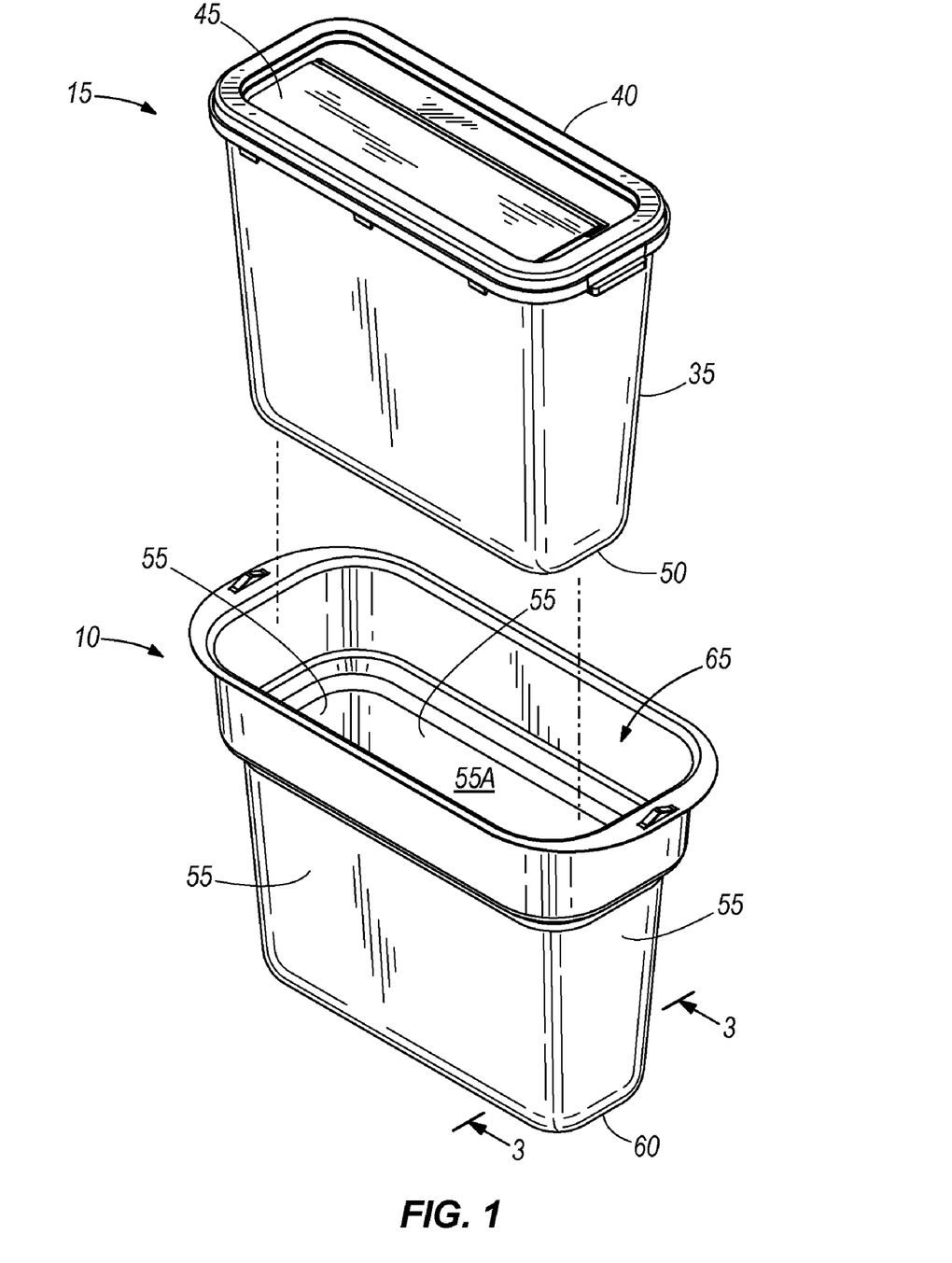
FIG. 1 is an exploded view of an exemplary sharps canister and receptacle according to one embodiment of the present invention.
Figure 2:
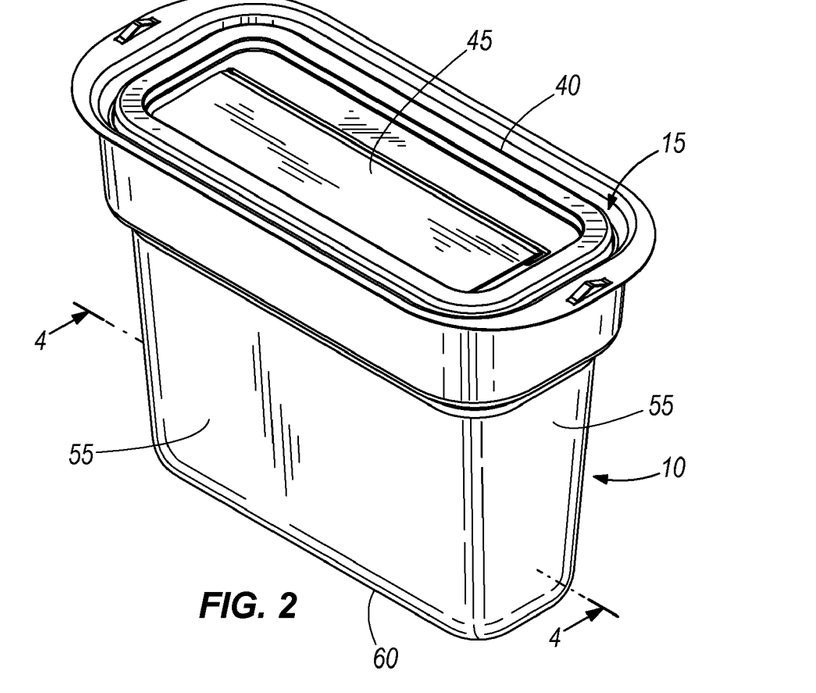
FIG. 2 is a perspective view of the sharps container and the receptacle shown in FIG. 1, and illustrating the sharps container positioned in the receptacle.
Figure 3:
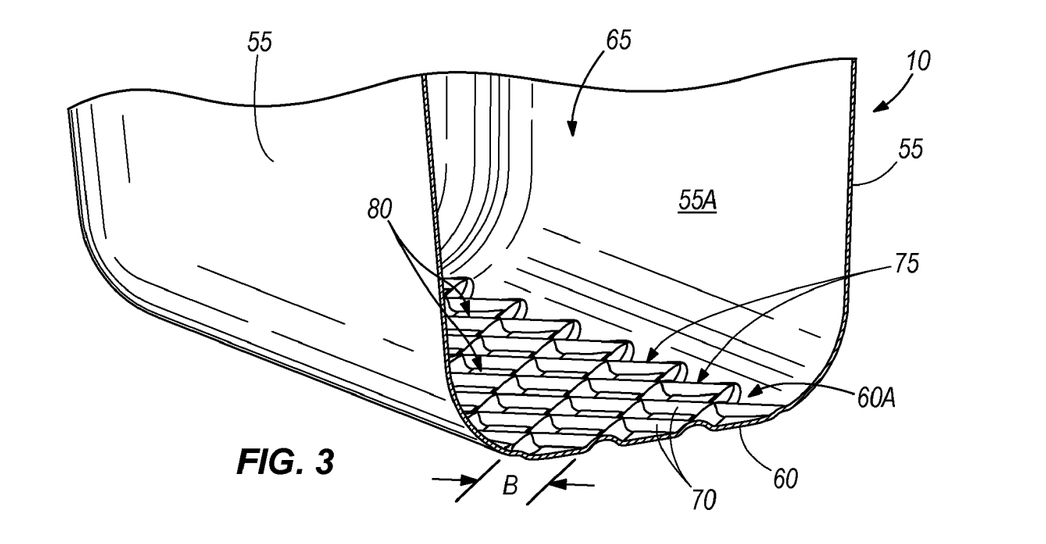
FIG. 3 is an enlarged perspective sectional view of a bottom wall of the receptacle taken along line 3-3 in FIG. 1.
Figure 4:
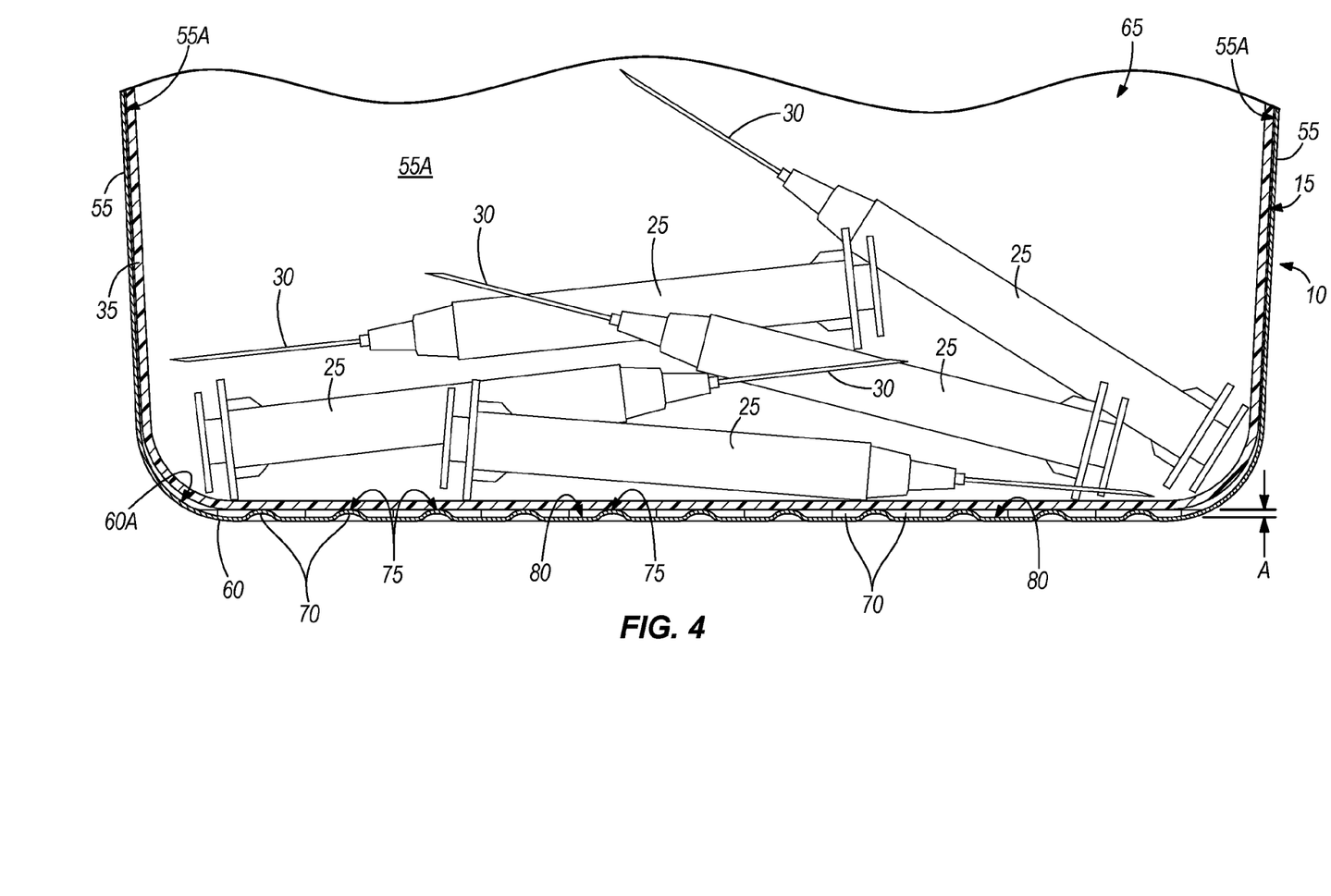
FIG. 4 is a sectional view of the sharps container and the receptacle taken along line 4-4 in FIG. 2, and illustrating the sharps container prior to sterilization.

FIGS. 1-5 illustrate a receptacle 10 for a sharps container 15 according to one embodiment of the invention. The sharps container 15 is placed in the receptacle 10 during a sterilization process in which the sharps container 15 and contents are melted. This process is further described below. FIGS. 1, 2 and 4 illustrate the sharps container 15, which receives medical and other infectious waste. Waste can include meltable items 25 (e.g., syringe bodies, tubes, handles, etc.) as well as sharps 30 (e.g., needles, scalpels, knives, blades, etc.), which generally do not melt. Some of the meltable items 25, such as syringe bodies, are generally made of a high melt flow polypropylene that will melt and flow easily when the sharps container 15 is heated. The sharps container 15 is generally made of plastic (e.g., polypropylene), which can be heated and thereby sterilized, although other materials can be used to form the sharps container 15. The sharps container 15 includes a body 35 for storing the medical waste. The sharps container 15 also includes a cover 40 that is mounted on top of the body 35 and that has a door 45 through which a user can place a used syringe horizontally. The door 45 guides syringes to fall into the body 35 in a typically horizontal manner such that the syringes rest in a generally horizontal position on the bottom 50 (FIG. 4) of the sharps container 15. The door also resists removal of sharps from the container. It is to be understood that other constructions of sharps containers fall within the scope of the invention. One possible alternative construction of a sharps container is shown in U.S. Pat. No. 5,605,245, which is incorporated herein by reference.

The receptacle or canister 10 holds the sharps container 15 and any contents (e.g., needles, syringes, scalpels, etc.) of the plastic sharps container 15 during melting and sterilization of the sharps container 15. The receptacle 10 includes side walls 55 and a bottom wall 60 (FIGS. 3-5) extending between the side walls 55. Each wall 55, 60 has respective interior surfaces 55A, 60A defining a space 65 for receiving the sharps container 15. The walls 55, 60 are formed to fit closely around the sharps container 15 to be melted. The receptacle 10 is made of metal and is preferably formed of a single piece of deep drawn metal using a process so there are no seams between the walls 55, 60 and so the side walls 55, in particular the interior surfaces 55A, have an adequate draft to remove the melted plastic sharps container 15 once cooled. It is to be understood that other processes can be used to form the receptacle 10, and that the receptacle 10 could be made of other heat-resistant materials.

Referring to FIG. 3, the receptacle 10 includes a crosshatch pattern of ribs 70 formed on the interior surface 60A of the bottom wall 60, although other patterns or geometric shapes can be used. The crosshatch ribs 70 are formed preferably by a stamping process and define on the interior surface 60A elevated areas 75 and recessed areas 80 between the elevated areas 75. In the illustrated embodiment, intersecting ribs 70 are perpendicular such that each recessed area 80 is square. In alternative embodiments, the recessed areas could have other shapes, such as being rectangles or parallelograms.

Figure 5:
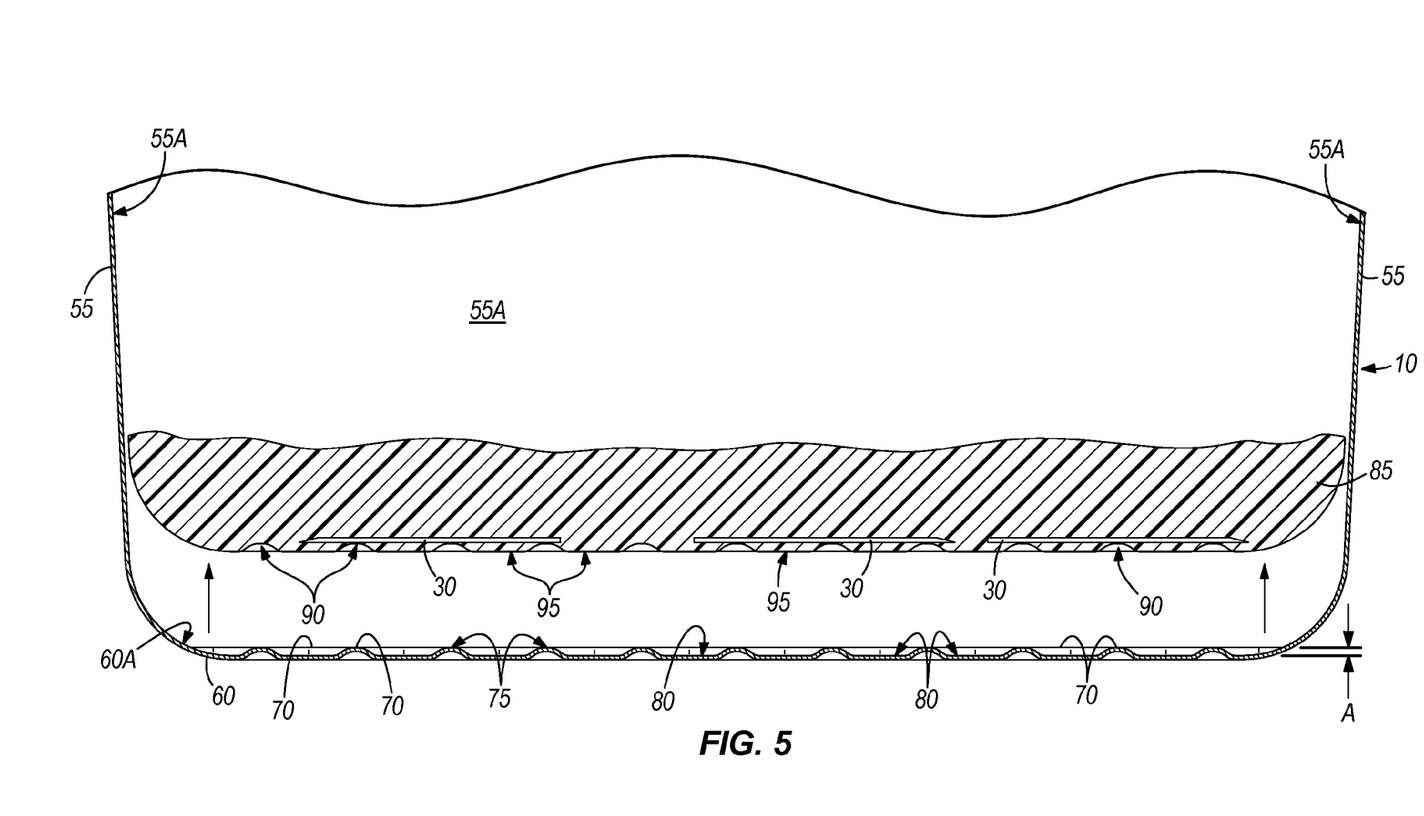
FIG. 5 illustrates a sectional view similar to FIG. 4 showing the sharps container sterilized and being removed from the receptacle.

The elevated areas 75 hold the sharps 30 above the recessed areas 80 during sterilization and melting of the sharps container 15. The elevated areas 75 are elevated above the recessed areas 80 a height "A" between approximately 0.04 inches and approximately 0.06 inches. The elevated areas 75 (or ribs 70) are spaced a horizontal distance "B" from one another so that the shortest needle or other sharp 30 is held by at least two elevated areas 75 during sterilization (e.g., melting of the sharps container 15). By way of example and as shown in FIG. 3, the horizontal distance "B" between adjacent ribs 70 or elevated areas 75 is approximately 0.5 inches. This spacing of the elevated areas 75 maintains the needles or other sharps 30 generally horizontal and spaced away from the recessed areas 80. Material from the melting sharps container 15 has the ability to flow underneath the sharps 30 supported on or above the elevated areas 75 via the recessed areas 80 and thus substantially encapsulate the sharps 30. The use of crosshatch ribs 70 to support sharps 30 away from outermost or exterior surfaces of the melting sharps container 15 greatly reduces or eliminates the possibility of a needle or other sharp 30 protruding from the resultant sterile body including the melted sharps container 15 and contents (FIG. 5). It should be understood that other configurations are within the scope of the invention. The height of the elevated areas and the spacing and shape of the ribs can be varied as long as sharps are generally held above the recessed areas during melting of the container 15, as further discussed below.

In use, sharps 30 and other medical waste are collected and stored in the plastic sharps container 15. To dispose of the sharps container 15 and contents, the container 15 is placed in the receptacle 10 so that the bottom 50 of the container 15 rests on or above the elevated areas 75 in the bottom of the receptacle 10. The configuration of the receptacle 10 could be such that bottom of the container 15 is held above the bottom of the receptacle 10, although in the illustrated construction the bottom of the container 15 rests on the ribs 70 or elevated areas 75. In either case, the bottom of the container 15 is held above the recessed areas 80. The receptacle 10 is then placed in an apparatus that heats the receptacle 10 and the container 15 to melt the container and render medical and other infectious waste substantially safe and sterile. An example of such an apparatus is manufactured by BioMedical Technology Systems (BMTS), is sold under the name Demolizer™ and is covered by U.S. Pat. No. 5,972,291, which is incorporated herein by reference.

Generally, the temperature and the amount of time used to heat the contents of the receptacle 10 are set to assure sterilization of the meltable contents 25 as well as the sharps 30, and to greatly reduce the volume of waste by melting the container and much of its contents. During this process, the meltable contents of the container flow into the recessed areas 80 of the receptacle 10, and the meltable contents melt and blend together with the melting sharps container 15 to form a melted body 85 (FIG. 5) of material encapsulating the sharps 30. Sharps 30 and other non-melting materials descend toward the bottom wall 60 of the receptacle 10 and rest either directly on the elevated areas 75 of the receptacle or on a layer of melted plastic between the sharps 30 and the elevated areas 75. In both cases, the sharps 30 are supported and maintained away from the recessed areas 80 and inside the melted body 85.

The sharps container 15 and meltable contents 25 are heated until sterilized. Then, the melted body 85 is cooled and removed from the receptacle 10. The ribs 70 on the interior surface 60A of the receptacle 10 form complementary crosshatch channels 90 (FIG. 5) in the bottom of the melted body 85. The sharps 30 are held on or above the crosshatch channels 90, and the material that flowed into the recessed areas 80 defines a barrier 95 between the sharps 30 and a user handling the melted body 85. A user should be able to safely remove the melted body 85 from the receptacle 10 and contact the barrier 95 without being struck by a sharp 30 (e.g., a needle). Thus, the sterilized melted body 85 can be removed from the receptacle 10 and safely disposed of in a non-infectious waste stream. The receptacle 10 can then be reused to heat and sterilize another sharps container.

Figure 6:
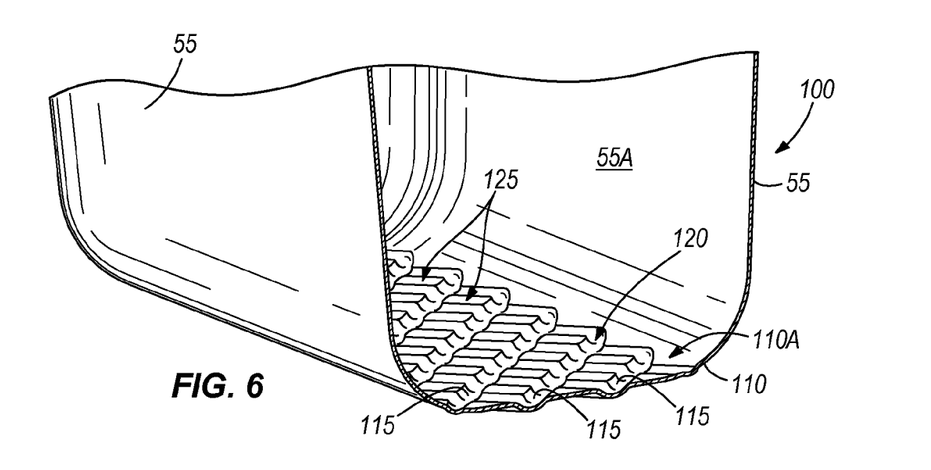
FIG. 6 is a perspective sectional view of a bottom wall of a receptacle according to another embodiment of the present invention.
Figure 7:
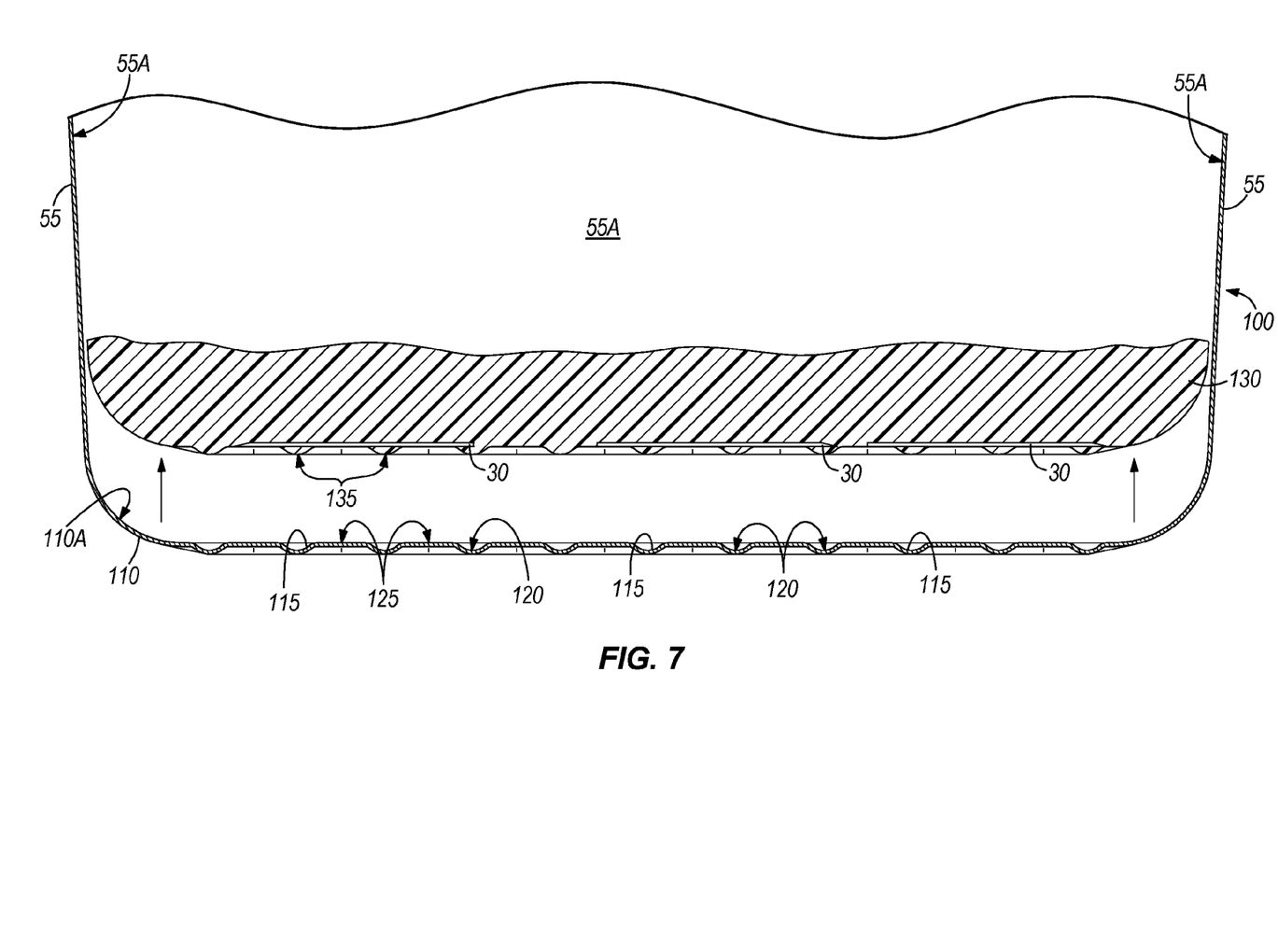
FIG. 7 is a sectional view of the receptacle shown in FIG. 6, and illustrating the exemplary sharps container melted and being removed from the receptacle.

FIGS. 6 and 7 illustrate an alternative receptacle 100 having a bottom wall 110. The bottom wall 110 includes crosshatch channels 115 formed in an interior surface 110A of the bottom wall 110. The crosshatch channels 115 are formed preferably by a stamping process and define recessed areas 120 and elevated areas 125 between the recessed areas 120. This pattern is essentially the reverse of the pattern of the receptacle 10. In other words, the same pattern that is stamped on the inside of the bottom of the receptacle 10 is stamped on the outside of the bottom of the receptacle 100. Therefore, the channels 115 have the same shape as the ribs 70, and the elevated areas 125 have the same shape as the recessed areas 80. The elevated areas 125 and recessed areas 120 function in the same way as the elevated areas 75 and recessed areas 80. The melted sharps container 15 and meltable contents 25 are cooled to form a melted body 130 having a barrier 135 of crosshatch ribs 140, which complement the crosshatch channels 115. The sharps 30 are held on the elevated areas 125 to inhibit the sharps 30 from protruding from the melted body 130 and the barrier 135 further inhibits a user from contacting any sharps 30.

Figure 8:
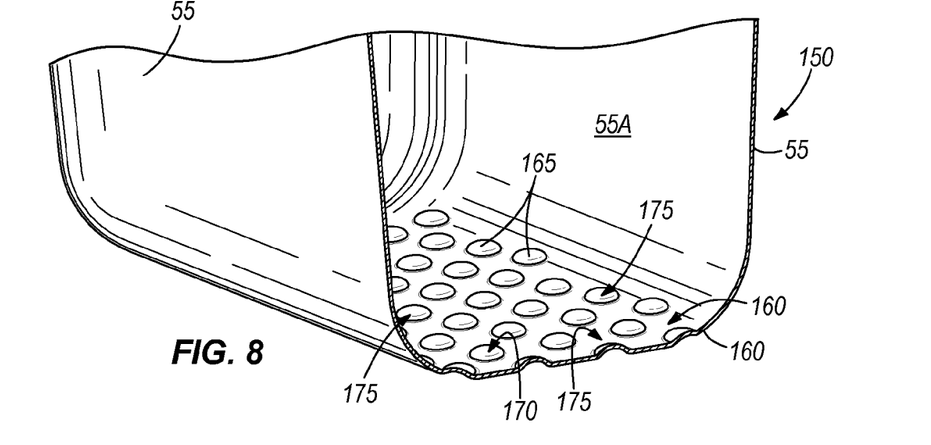
FIG. 8 is a perspective sectional view of a bottom wall of a receptacle according to another embodiment of the present invention.

FIG. 8 illustrates yet another alternative receptacle 150 having a bottom wall 160. The bottom wall 160 includes bumps 165 formed on an interior surface 160A of the bottom wall 160. The bumps 165 are formed preferably by a stamping process. The bumps 165 define elevated areas 170 on the interior surface 160A, with recessed areas 175 between the bumps 165. Each bump 165 has a substantially hemispherical shape and is spaced from the other bumps 165 to form a particular pattern, although in other constructions the bumps 165 can be positioned in an irregular pattern. In any event, the bumps are positioned such that at least two bumps 165 hold the sharps 30 above the recessed areas 175 during sterilization and melting of the sharps container 15.

Figure 9:
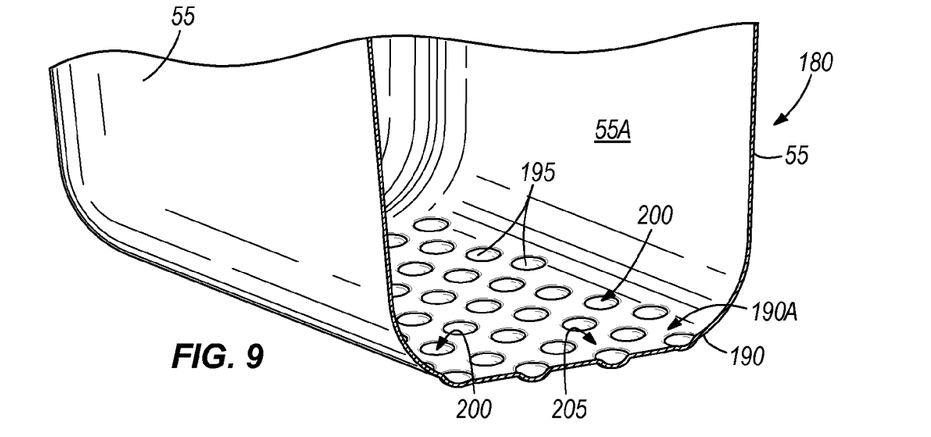
FIG. 9 is a perspective sectional view of a bottom wall of a receptacle according to another embodiment of the present invention.

FIG. 9 illustrates still another alternative receptacle 180 having a bottom wall 190. The bottom wall 190 includes dimples 195 formed in an interior surface 190A of the bottom wall 190. The dimples 195 are formed preferably by a stamping process. The dimples 195 define recessed areas 200 in the interior surface 190A, with elevated areas 205 between the dimples 195. Each dimple 195 has a substantially hemispherical shape and is spaced from the other dimples 195 to form a particular pattern, although in other constructions the dimples 195 can be positioned in an irregular pattern. In any event, the dimples 195 are positioned such that at least two elevated areas 205 hold the sharps 30 above the recessed areas 200 during sterilization and melting of the sharps container 15.

An existing receptacle for an apparatus can be modified to include a texture (e.g., crosshatch ribs or channels, dimples, bumps, etc.). For example, the texture can be stamped post manufacture of the receptacle.

Figure 10:
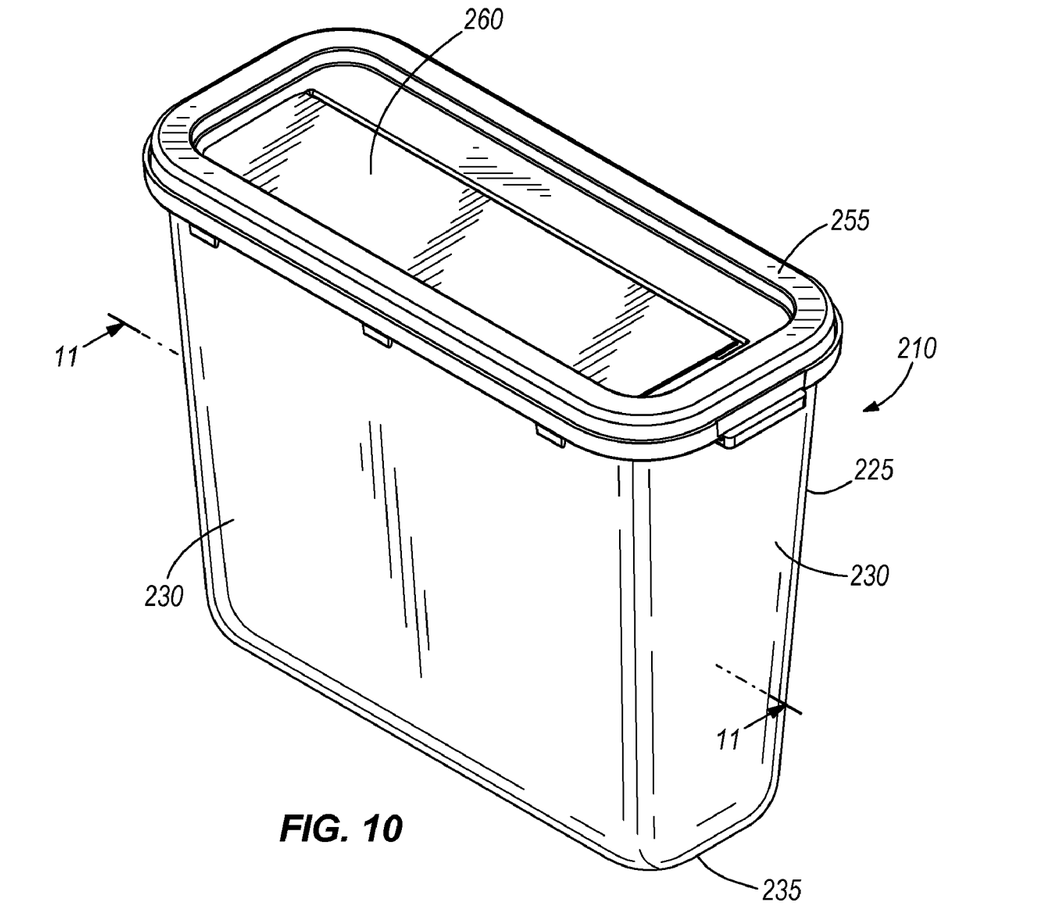
FIG. 10 is a perspective view of an exemplary sharps container according to another embodiment of the present invention.
Figure 11:
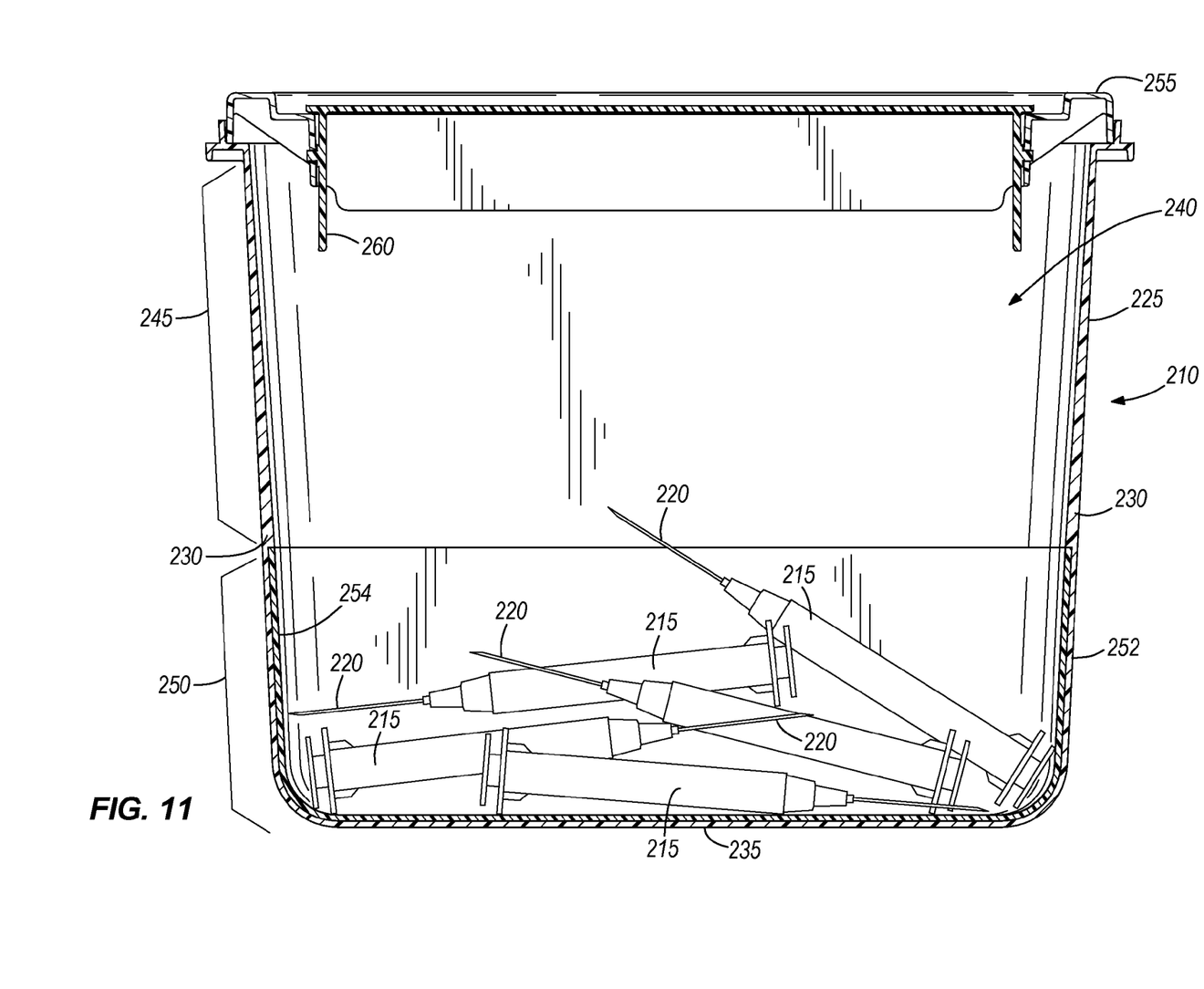
FIG. 11 is a sectional view of the sharps container taken along line 11-11 in FIG. 10.
Figure 12:
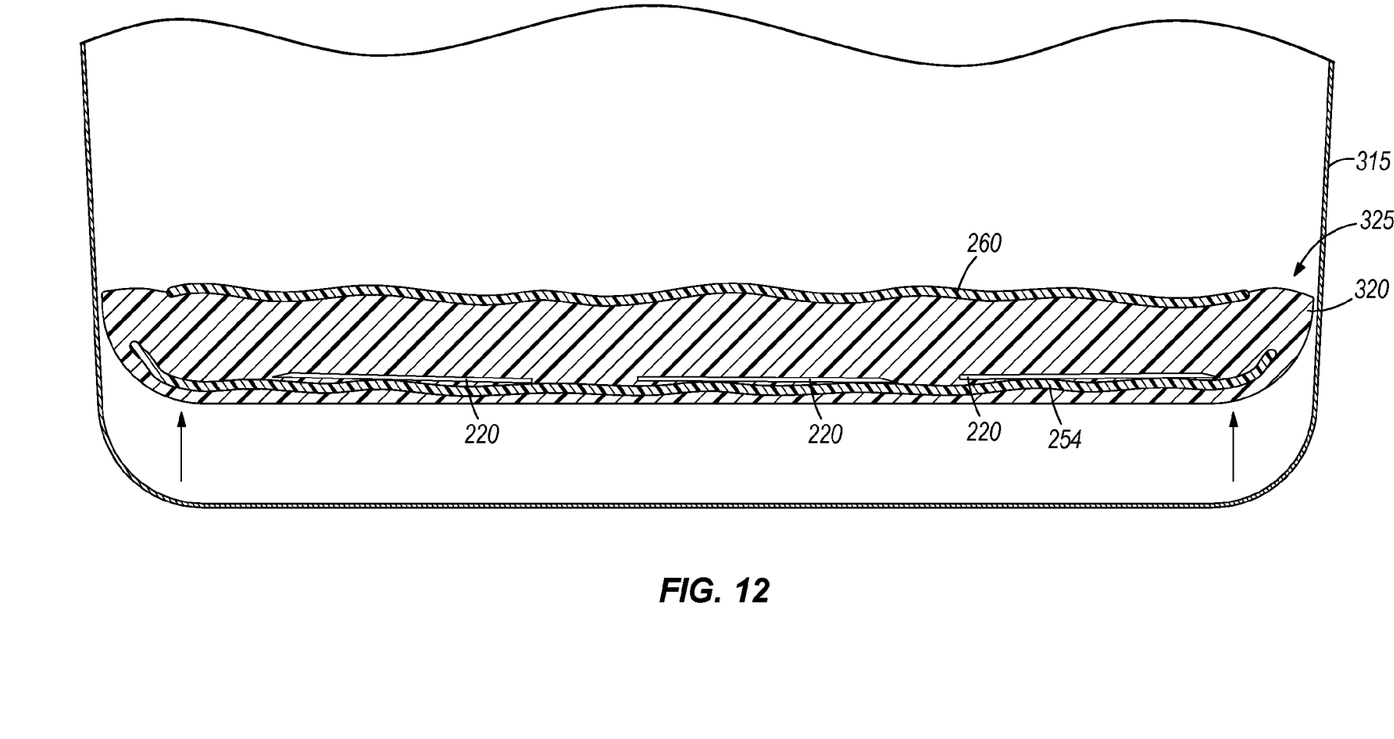
FIG. 12 illustrates a sectional view of the sharps container shown in FIG. 11 being removed from a receptacle after sterilization.

FIGS. 10-12 illustrate a multi-material sharps container 210 according to another embodiment of the invention. The sharps container 210 receives and stores medical and other infectious waste 215 (including sharps 220), and is then heat treated to sterilize and dispose of the sharps container 210 and contents 215. Referring to FIG. 11, the sharps container 210 includes a body 225 having side walls 230 and a bottom wall 235 extending between the side walls 230. The body 225 defines a space 240 for receiving the medical waste 215. The body 225 has an upper portion 245 and a lower portion 250. The upper portion 225 includes the upper portions of the side walls 230, and the lower portion 250 includes the lower portions of the side walls 230 and the bottom wall 235. Generally, the body 225 is made of two different materials, although the body 225 may be formed of more than two materials. The upper portion 245 is made entirely of a first material, which has a melting temperature less than the working temperature of the sterilization process so as to melt readily during the sterilization process. The lower portion 250 is made of two materials. Specifically, the lower portion 250 has an outer part 252 that is formed integrally with the upper portion 245 and is made of the first material. The lower portion 250 also has an inner part 254 made of a second material that melts at a slower rate than the first material. By this it is meant that the second material either does not melt at all or does not flow nearly as easily as the first material or remains viscous at the processing temperature. The inner part 254 is cup-shaped and forms the inner part of the bottom wall 235 and the inner part of the side walls 230 up to the upper portion 245. In other constructions, the inner part 254 may not include a portion of the side walls 230. In other constructions, the lower portion 250 can be made entirely of the second material. The cup-shaped inner part 254 has a height that will allow the sharps to remain below the top of the non-melting second material during the sterilization process.

In the illustrated construction, the first material is a high melt flow polyolefin plastic having a melt flow rate of approximately 30 MF. Hereinafter, "MF" refers to melt flow rate and is measured in grams/10 minutes at a temperature of 230 degrees Celsius with a mass of 2.16 kilograms. In other constructions, the first material is any polymer that melts during the sterilization process. Many suitable second materials can be used. The second material could be a thermoset such as Mylar. The second material could also be a polyolefin like the first material, but having a substantially lower melt flow rate, preferably between approximately 4 MF and approximately 10 MF. The second material could also be a resin having a melting temperature that is greater than the processing or working temperature used to sterilize the sharps container 210. The second material could also be a polyolefin with one or more additives, such as glass fibers, glass balls, calcium carbonate or any substance that will cause the material to be more viscous or to have a higher melt strength so as to inhibit penetration of sharps when heating the sharps container. The second material could also be a cross-linked polyethylene. The cup-shaped inner part 254 would be molded and then cross-linked using radiation or other means to inhibit the contained sharps from protruding though the lower portion 250.

The sharps container 210 also includes a cover 255 on top of the body 225. The cover 255 has a door 260 to allow insertion of the medical waste into the space 240 of the body 225 and to resist removal of the medical waste 215 from the space 240. In the illustrated construction, the door 260 is made of the second material, which has a low melt flow rate. Thus, the door 260 melts at a slower rate than the upper portion 245. The remainder of the cover 255 is made of the first material (or another material with a high melt flow rate) such that as the sharps container 210 is heated, the non-door portion of the cover 255 melts and causes the door 260 to fall on top of the melt. In other constructions, the door 260 can be formed of any material that has a melt flow rate less than the melt flow rate of the upper portion 245. In yet other constructions, any part of the cover 255 can be made of a material having a melt flow rate less than that of the upper portion 245.

Figure 13:
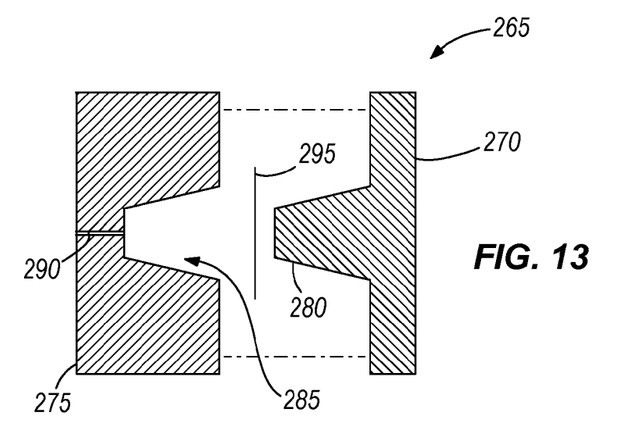
FIG. 13 illustrates a manufacturing process for the sharps container shown in FIG. 10.
Figure 14:
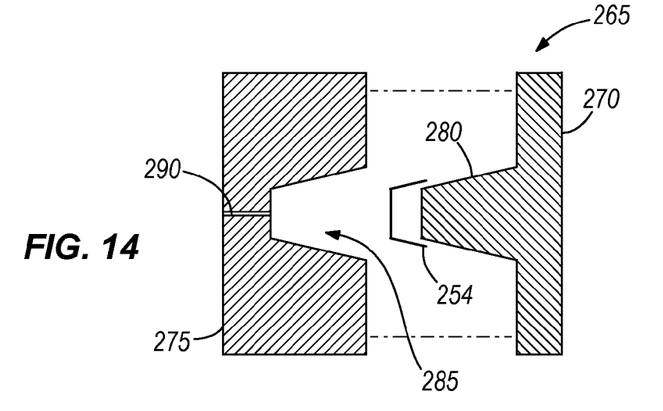
FIG. 14 illustrates another manufacturing process for the sharps container shown in FIG. 10.
Figure 15:
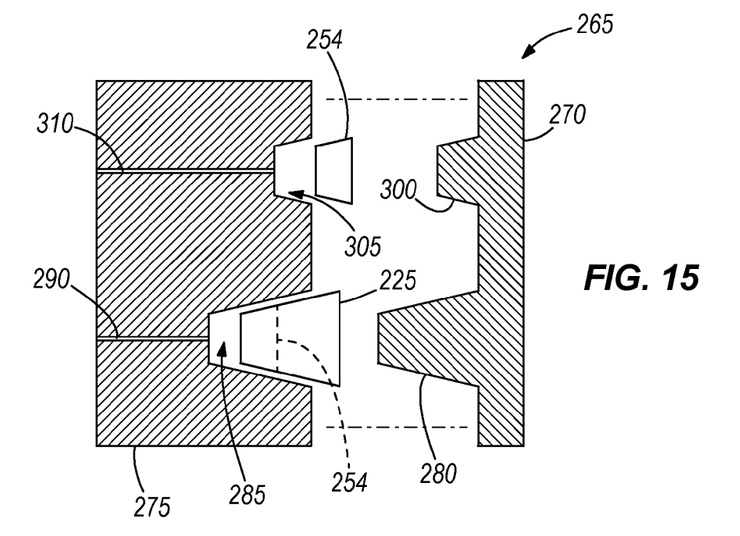
FIG. 15 illustrates yet another manufacturing process for the sharps container shown in FIG. 10.

The body 225 of the sharps container 210 is preferably manufactured using an injection molding process. FIGS. 13-15 illustrate injection molding processes that can be used to form the sharps container 210 illustrated in FIGS. 10-12. Each injection molding process uses a mold 265 having two parts or sides 270, 275.

Referring to the injection molding process illustrated in FIG. 13, the first side 270 of the mold 265 includes a core 280 that fits into a recess 285 in the second side 275 to define a cavity that is filled with the first and second materials to form the body 225. The second side 275 of the mold 265 also has a gate 290 through which the first material is injected into the cavity around the second material. A sheet 295 of the second material is placed between the first and second sides 270, 275 of the mold 265 when the mold 265 is open, as shown in FIG. 13. The mold 265 is then closed and the core 280 presses the sheet 295 of the second material into the cavity 285 to form the cup-shaped inner part 254 (FIG. 11). Then the first material is injected through the gate 290 to fill the cavity. As the first material enters the cavity, the first material forces the cup-shaped second material against the core 280. The first material is injected into the cavity and around the cup-shaped second material until the body 225 is fully formed.

FIG. 14 illustrates another injection molding process to form the body 225. The injection molding process is similar to the injection molding process shown in FIG. 13; therefore, like structure is identified by the same reference numerals. In the injection molding process shown in FIG. 14, the second material is pre-formed into the cup-shaped inner part 254 using a thermal forming process. The pre-formed cup is placed in the cavity and then the first material is injected as described above.

FIG. 15 illustrates yet another injection molding process. The injection molding process is similar to the injection molding process shown in FIG. 14; therefore, like structure is identified by the same reference numerals. The injection molding process shown in FIG. 15 is a two-shot injection molding process. The first side 270 of the mold 265 includes a second or upper core 300 and the second side 275 of the mold 265 includes a second or upper recess 305. The core 300 fits into the recess 305 to define an upper cavity having the shape of the cup-shaped inner part 254. During the first shot of the process, the mold 265 is closed and the second material is injected through an upper gate 310 into the upper cavity to form the cup-shaped part 254. Then the mold is opened, the cup-shaped part is placed over the core 280, and the mold is again closed. During the second shot of the process, the first material is injected through the gate 290 to fill the lower cavity in the same manner as described above.

It should be understood that other injection molding processes can be used to form the body of the sharps container 210. For example, it is contemplated that the two-shot injection molding process shown in FIG. 15 can be performed using two different molds: a first mold for forming the inner part 254 and a second mold for molding the first material to form the body 225.

In another example, the inner part or cup 254 is made in a first injection molding machine using a cross linkable resin as the second material. The cup is then treated, such as with an electron beam, to cross link the polymer. Then the cup is placed in a second molding machine in which it is over-molded with the first material outside the second material.

The body of the sharps container 210 can also be formed using a co-injection molding process. The mold is closed and the first material is injected to partially fill the mold. The second material is the injected to form the cup. Then the first material is injected to overmold the second material.

In other constructions, the body 225 can be formed having the cup-shaped second material outside of the first material.

The sharps container 210 is used as follows. Medical waste 215 is collected in the sharps container 210. During the sterilization process, the sharps container 210 is heated in a receptacle or canister 315 (FIG. 12) in the same manner as described above. The receptacle 315 differs from the above-described receptacles in that the receptacle 315 has a flat bottom. As the sharps container 210 is heated, the upper portion 245 melts and collapses on the contents of the sharps container 210. Some of the contents 215 are formed of meltable materials which also melt. The upper portion 245 and some of the meltable contents blend together to form a blended mixture 320, while the sharps 220 descend through the blended mixture 320 and rest in the cup-shaped inner part 254. FIG. 12 illustrates the blended mixture after cooling. The inner part 254 melts at a slower rate than the upper portion 245 and meltable contents. Thus, as the sharp container 210 is heated, the blended mixture 320 encapsulates the inner part 254 and the sharps 220 supported on or above the bottom wall 235. Generally, the inner part 254 remains a relatively rigid and impenetrable structure so as to inhibit sharps 220 from protruding from the resultant sterile body 325 (FIG. 12).

Also, as the sharps container 210 is heated, the cover 255 (including the door 260) collapses on the blended mixture 320 inside the receptacle 315. The door 260 exhibits the same or similar thermal properties as the inner part 254. As the cover 255 collapses, the door 260 descends and acts as a blanket covering any sharps 220 that may be pointed upwards and further inhibiting sharps 220 from protruding from the resultant sterile body 325.

The resultant sterile body 325 can be safely removed from the receptacle 315 and disposed of in the non-infectious waste stream.

Various features and advantages of the invention are set forth in the following claims.

What is claimed is:

1. A method of collecting and disposing of sharps, the method comprising:
    collecting the sharps in a meltable sharps container having a bottom;
    providing a receptacle including a side wall and a bottom wall having respective interior surfaces defining a space, a plurality of recessed areas in the interior surface of the bottom wall, and a plurality of elevated areas on the interior surface of the bottom wall;
    placing the sharps container in the space of the receptacle so that the bottom of the sharps container is above or supported by the elevated areas;
    melting the sharps container in the receptacle such that as the sharps container melts, material from the sharps container flows into the recessed areas and the elevated areas hold the sharps above the recessed areas, so as to inhibit the sharps from protruding through the melted sharps container;
    removing the melted sharps container from the receptacle; and
    disposing of the melted sharps container and sharps.

2. The method of claim 1, wherein placing the sharps container in the receptacle includes resting the bottom of the sharps container on the elevated areas.

3. The method of claim 1, wherein melting the sharps container includes encapsulating the sharps with material from the melting sharps container as the sharps rest on the elevated areas.

4. The method of claim 1, further comprising supporting the sharps on at least two of the elevated areas while melting the sharps container.

5. The method of claim 1, wherein melting the sharps container includes forming a barrier in the melting sharps container with the material in the recessed areas such that the barrier holds the sharps inside the melted sharps container.

6. The method of claim 1, wherein melting the sharps container includes forming a crosshatch pattern in the bottom of the sharps container.

7. The method of claim 1, wherein melting the sharps container includes forming a plurality of dimples in the bottom of the sharps container.

8. The method of claim 1, wherein melting the sharps container includes forming a plurality of bumps on the bottom of the sharps container.

9. The method of claim 1 and further comprising providing the sharps container with a cover positioned on the body and having a door, and heating the sharps container such that the door melts at a slower rate than a lower portion of the container and descends toward and covers the sharps so as to inhibit the sharps from protruding through the door.

10. A method of collecting and disposing of sharps, the method comprising:
   collecting the sharps in a meltable sharps container having a bottom;
   providing a receptacle including a side wall and a bottom wall having respective interior surfaces defining a space, a plurality of recessed areas in the interior surface of the bottom wall, and a plurality of elevated areas on the interior surface of the bottom wall;
   placing the sharps container in the space of the receptacle so that the bottom of the sharps container is above or supported by the elevated areas;
   melting the sharps container in the receptacle such that as the sharps container melts, material from the sharps container flows into the recessed areas, the elevated areas hold the sharps above the recessed areas, and the sharps container forms a melted body encapsulating and supporting the sharps, so as to inhibit the sharps from protruding through the melted body;
   removing the melted body from the receptacle; and
   disposing of the melted body.

11. The method of claim 10, wherein melting the sharps container includes the sharps and sharps container blending together to form a melted body.

12. The method of claim 10, wherein placing the sharps container in the receptacle includes resting the bottom of the sharps container on the elevated areas.

13. The method of claim 10, further comprising supporting the sharps on at least two of the elevated areas while melting the sharps container.

14. The method of claim 10, wherein melting the sharps container includes forming a barrier in the melting sharps container with the material in the recessed areas such that the barrier holds the sharps inside the melted sharps container.

15. The method of claim 10, wherein melting the sharps container includes forming a crosshatch pattern in the bottom of the sharps container.

16. The method of claim 10, wherein melting the sharps container includes forming a plurality of dimples in the bottom of the sharps container.

17. The method of claim 10, wherein melting the sharps container includes forming a plurality of bumps on the bottom of the sharps container.

18. The method of claim 10 and further comprising providing the sharps container with a cover positioned on the body and having a door, and heating the sharps container such that the door melts at a slower rate than a lower portion of the container and descends toward and covers the sharps so as to inhibit the sharps from protruding through the door.

19. A method of collecting and disposing of sharps, the method comprising:
   collecting the sharps in a meltable sharps container having a bottom;
   providing a receptacle including a side wall and a bottom wall having respective interior surfaces defining a space, a plurality of recessed areas in the interior surface of the bottom wall, and a plurality of elevated areas on the interior surface of the bottom wall;
   placing the sharps container in the space of the receptacle so that the bottom of the sharps container is above or supported by the elevated areas;
   melting the sharps container in the receptacle such that as the sharps container melts, material from the sharps container flows into the recessed areas, any meltable contents melt and blend together with the melting sharps container to form a melted body of material, sharps and other non-melting materials descend toward the bottom wall of the receptacle and rest either directly on the elevated areas or on a layer of melted plastic between the sharps and the elevated areas, and sharps are supported and maintained away from the recessed areas and inside the melted body;
   removing the melted body from the receptacle; and
   disposing of the melted body.

20. The method of claim 18, wherein placing the sharps container in the receptacle includes resting the bottom of the sharps container on the elevated areas.

21. The method of claim 18, further comprising supporting the sharps on at least two of the elevated areas while melting the sharps container.

22. The method of claim 18 and further comprising providing the sharps container with a cover positioned on the body and having a door, and heating the sharps container such that the door melts at a slower rate than a lower portion of the container and descends toward and covers the sharps so as to inhibit the sharps from protruding through the door.

* * * * *